US005539019A

United States Patent [19]

Suskind et al.

[11] Patent Number: 5,539,019
[45] Date of Patent: Jul. 23, 1996

[54] HIGH PERFORMANCE ABSORBENT PARTICLES AND METHODS OF PREPARATION

[75] Inventors: Stuart Suskind, Wayne, Pa.; Leonard Pearlstein, 1441 Waverly Ave., Gladwyne, Pa. 19035

[73] Assignee: Leonard Pearlstein, Gladwyne, Pa.

[21] Appl. No.: 456,920

[22] Filed: Jun. 1, 1995

Related U.S. Application Data

[63] Continuation of Ser. No. 283,559, Aug. 1, 1994.
[51] Int. Cl.$^6$ .............................. C08L 33/02; C08K 3/34; C08K 3/00; B32B 27/02
[52] U.S. Cl. ........................ 523/201; 523/202; 523/204; 428/407
[58] Field of Search .................................. 604/368, 372; 523/200, 201, 202, 204, 205, 209, 203; 428/407

[56] References Cited

U.S. PATENT DOCUMENTS

| | | |
|---|---|---|
| Re. 32,649 | 4/1988 | Brandt et al. . |
| Re. 33,839 | 3/1992 | Chmelir et al. . |
| 3,544,500 | 12/1970 | Osmond ................................ 523/209 |
| 3,932,322 | 1/1976 | Duchane . |
| 3,935,363 | 1/1976 | Burkholder et al. . |
| 3,992,558 | 11/1976 | Smith-Johannsen et al. .......... 428/407 |
| 4,058,124 | 11/1977 | Yen et al. . |
| 4,081,402 | 3/1978 | Levy et al. . |
| 4,093,776 | 6/1978 | Aoki et al. . |
| 4,135,943 | 1/1979 | Morishita et al. . |
| 4,217,901 | 8/1980 | Bradstreet et al. . |
| 4,239,043 | 12/1980 | Gellert . |
| 4,242,251 | 12/1980 | Aishima et al. . |
| 4,245,005 | 1/1981 | Regnier et al. . |
| 4,286,082 | 8/1981 | Tsubakimoto et al. . |
| 4,295,987 | 10/1981 | Parks . |
| 4,324,247 | 4/1982 | Aziz . |
| 4,324,314 | 8/1982 | Radel et al. . |
| 4,333,464 | 6/1982 | Nakano . |
| 4,340,706 | 7/1982 | Obayashi et al. . |
| 4,392,908 | 7/1983 | Dehnel . |
| 4,418,163 | 11/1983 | Murakami et al. . |
| 4,446,261 | 5/1984 | Yamasaki et al. . |
| 4,454,055 | 6/1984 | Richman et al. . |
| 4,467,012 | 8/1984 | Pedersen et al. . |
| 4,474,852 | 10/1984 | Craig . |
| 4,500,670 | 2/1985 | McKinley et al. . |
| 4,507,438 | 3/1985 | Obayashi et al. . |
| 4,535,098 | 8/1985 | Evani et al. . |
| 4,587,308 | 5/1986 | Makita et al. . |
| 4,634,440 | 1/1987 | Widlund et al. . |
| 4,646,730 | 3/1987 | Schonfeld et al. . |
| 4,655,757 | 4/1987 | McFarland et al. . |
| 4,666,983 | 5/1987 | Tsubakimoto et al. . |
| 4,683,274 | 7/1987 | Nakamura et al. . |
| 4,732,968 | 3/1988 | Obayashi et al. . |
| 4,735,987 | 4/1988 | Morita et al. . |
| 4,742,086 | 5/1988 | Masamizu et al. . |
| 4,771,086 | 9/1988 | Martn ...................................... 523/205 |
| 4,777,232 | 10/1988 | Heidel . |

(List continued on next page.)

FOREIGN PATENT DOCUMENTS

| | | |
|---|---|---|
| 0457660 | 11/1991 | European Pat. Off. . |
| WO91/15177 | 11/1991 | WIPO . |
| WO93/17066 | 9/1993 | WIPO . |
| WO93/24153 | 12/1993 | WIPO . |

Primary Examiner—David H. Willse
Assistant Examiner—Dennis Ruhl
Attorney, Agent, or Firm—Finnegan, Henderson, Farabow, Garrett & Dunner

[57] ABSTRACT

A high performance absorbent particulate composition and a method of preparation in which non-colloidal solid filler core is substantially encapsulated within a bounding layer of hydrogel forming polymer is disclosed. In preferred embodiments, the size of the solid filler core is about 10 to about 1500 microns contributing about 20% to about 90% by weight of the composition. The particles of the present invention provide rapid absorption of a large volume of aqueous fluids. A wide range of performance properties are achieved through selection of the filler core and the polymer.

21 Claims, 3 Drawing Sheets

U.S. PATENT DOCUMENTS

| | | |
|---|---|---|
| 4,783,510 | 11/1988 | Saotome . |
| 4,795,762 | 1/1989 | Diamantoglou et al. . |
| 4,800,103 | 1/1989 | Jeffs . |
| 4,880,870 | 11/1989 | Zimmermann et al. . |
| 4,888,238 | 12/1989 | Katz et al. . |
| 4,914,066 | 4/1990 | Woodrum . |
| 4,944,735 | 7/1990 | Mokry . |
| 4,950,264 | 8/1990 | Osborn, III . |
| 4,952,550 | 8/1990 | Wallach et al. . |
| 4,977,192 | 12/1990 | Martineu et al. ............... 521/56 |
| 4,992,326 | 2/1991 | Dabi . |
| 5,019,063 | 5/1991 | Marsan et al. . |
| 5,032,425 | 7/1991 | Liusey et al. ................. 523/205 |
| 5,061,259 | 10/1991 | Goldman et al. . |
| 5,074,856 | 12/1991 | Coe et al. . |
| 5,078,909 | 1/1992 | Shigeta et al. . |
| 5,079,004 | 1/1992 | Blank et al. . |
| 5,082,723 | 1/1992 | Gross et al. . |
| 5,118,719 | 6/1992 | Lind . |
| 5,145,906 | 9/1992 | Chambers et al. . |
| 5,147,343 | 9/1992 | Kellenberger . |
| 5,147,921 | 9/1992 | Mallo . |
| 5,154,713 | 10/1992 | Lind . |
| 5,180,622 | 1/1993 | Berg et al. . |
| 5,180,798 | 1/1993 | Nakamura et al. . |
| 5,188,899 | 2/1993 | Matsumoto et al. . |
| 5,196,456 | 3/1993 | Nguyen et al. . |
| 5,196,473 | 3/1993 | Valenta et al. . |
| 5,230,958 | 7/1993 | Dabi . |
| 5,250,642 | 10/1993 | Ahmed et al. . |
| 5,258,448 | 11/1993 | Mallo et al. . |
| 5,264,471 | 11/1993 | Chmelir . |
| 5,286,770 | 2/1994 | Bastioli et al. . |
| 5,300,358 | 4/1994 | Evers . |

HIGH PERFORMANCE ABSORBENT PARTICLES AND METHODS OF PREPARATION

This is a continuation of application Ser. No. 08/283,559, filed Aug. 1, 1994.

BACKGROUND OF THE INVENTION

The present invention relates to absorbent particles and the use of such particles in absorbent articles such as disposable diapers and sanitary pads.

Generally, absorbent articles are designed to have at least three distinct layers:

(1) a liquid pervious topsheet of bonded fibers usually referred to as a non-woven or an apertured film;

(2) an absorbent core containing mainly hydrophilic fibers such as a loose mat of pulp fibers usually referred to as "fluff" often contributing as much as 90% of the overall thickness of the article; and (3) a liquid barrier outer film which is usually a polyolefin at a thickness of about 0.5–1.5 mil.

Fluids passing through the topsheet are distributed by the pulp fibers and are held within the interstices of the pulp web. Increases in pulp content generally lead to increases in the absorbent capacity of these devices. In light of the relatively low cost of pulp, absorbent articles are often designed with thick, bulky cores to provide high capacity in the absorbent article. The inherent disadvantages of such bulkiness are lack of comfort, visibility through clothing, and the inability of the article to conform to the shape of the body leading to unpredictable shifting and even fluid leakage. Importantly, these bulky items require precious storage space in distribution and in ultimate usage.

The development of superabsorbent polymers (SAP) which absorb at least 3–4 times as much fluid as pulp, has lead to the successful design of much thinner products in which a substantial portion of the fluff has been replaced by SAP granules. While the consumer has accepted and even preferred these thinner articles, certain performance attributes are still not satisfactory and improvements are sought. For example, leakage is still one of the most important and the most critical deficiency remaining in disposable diaper design.

One approach taken to solve this problem has been to incorporate yet more SAP into the product. It is not uncommon in ultra-thin diapers to use as much as 6–15 grams of SAP granules per diaper accounting for up to 60% by weight of the absorbent core in order to achieve significant reductions in bulk or thickness and still provide needed performance.

SAP, generally, are polymeric materials containing water insoluble long chain molecules with a low degree cross-linking which are capable of forming hydrogel networks. In the presence of water or aqueous solutions such as body fluid, these hydrogel networks swell into a soft, resilient "jelly-like" material. When the swelling fluid is 0.9% saline, urine, or synthetic urine, these polymers may ultimately swell up to about 25–40 times their original weight. On the other hand, pulp fibers have a capacity to swell by a factor of only about 7–10 times by comparison.

The SAP materials are typically produced as granules which may then be mixed with pulp fibers during the formation of the absorbent core. Thus, with such highly absorbent granular material, it becomes possible to design and produce absorbent articles with roughly ½ to ⅓ of the bulkiness of the 100% pulp core. Reduction in volume of this nature is the subject of numerous U.S. Patents including for example, U.S. Pat. Nos. 4,950,264 (Osborn); 4,467,012 (Pederson); and 4,217,901 (Bradstreet), all incorporated in their entirety by reference herein.

There is unfortunately a disadvantage associated with this improvement. For while SAP is about three-fold more absorbent than pulp, its cost is about four-fold higher. It is not surprising, therefore, that considerable effort has been dedicated toward maximizing or optimizing the cost effectiveness of the superabsorbent. These efforts are the subject of numerous U.S. patents. For example, particle size, modules, degree of neutralization, and residual monomers, are discussed in U.S. Pat. Nos. Re. 32,649 (Brandt) and 5,061,259 (Goldman et al.), both incorporated in their entirety by reference herein.

Furthermore, technical contributions were reported at the Advances in Superabsorbent Polymers Symposium, Fall Meeting 1993 of the American Chemical Society, as published in the Proceedings of the Division of Polymeric Materials: Science and Engineering (Masuda, p. 464; Nagorski, p. 560), incorporated herein by reference.

Prior to the trend toward thinner diapers, SAP was designed initially for maximum capacity and later with increased cross-linking for improved gel stability and absorbency under a load. With the trend toward thinner construction, the speed of liquid acquisition and distribution are also important properties. Accordingly, while SAP particles usually swell to capacity after about one hour exposure to fluid, the uptake rate during the first ten to twenty minutes is now considered critical.

It has been recognized that the rate of absorption could be increased through higher cross-link density of the SAP since the resulting increase in gel strength helps to maintain particle identity during swelling thus reducing particle coalescence. The effect of the latter phenomenon known as "gel blocking" is to block the open spaces in the web, causing a decrease in the rate of absorption. The undesirable drawback with increased cross-linking is the associated reduction in fluid capacity. In U.S. Pat. Nos. 4,587,308 (Makita) and 4,507,438 (Obayashi) (both incorporated in their entirety by reference herein), particles are subjected to cross-linking on the particle surface thereby increasing surface gel strength without compromising the swell capacity within the particle.

In U.S. Pat. No. 3,932,322 (Duchane) (incorporated in its entirety by reference herein), the tendency for particle agglomeration is reduced by admixing a small amount of very fine inorganic oxide particles which tend to coat the SAP particles.

The problem of reduced rate due to blocking of fluid is also addressed in U.S. Pat. No. 5,147,343 (Kellenberger) (incorporated in its entirety by reference herein), wherein the size of the superabsorbent particle is selected to be larger than the pore size of the absorbent core (i.e., at least about 100 microns). This design feature is claimed to provide improved absorbency under a load or under the weight of the user's body.

The importance of particle size is further taught in U.S. Pat. No. 5,180,622 (Berg et al.) (incorporated in its entirety by reference herein). This patent, more specifically, discloses that surface area of the particles controls the rate of fluid uptake. Since small particles have the more favorable ratio of surface area to mass, theory would predict a higher absorption rate with relatively small particles, i.e., about 50 µm. In fact, due to ease of packing, particles this size tend to form a mass of coagulated gel and fluid and flow is impeded by their "gel blocking." In the Berg et al. patent, the trade-off between fluid uptake and gel coagulation is resolved through a process which chemically links small particles into a larger cluster or agglomerate. These new particles have significantly higher swell rates than the precursor particles based on the high surface to mass ratio; however, this benefit is offset to some degree by increased processing cost.

Another approach to solving the trade-off problem is to simply use larger quantities of larger particles; the drawback here is that increased volumes of SAP create additional expense for the manufacturer. Further, the greater fluid capacity realized with more SAP is usually not utilized.

It is also desirable to provide a simple and new means by which average particle size and particle size distribution may be controlled.

SUMMARY OF INVENTION

In light of the high cost of superabsorbent polymers and the need to find efficient and improved ways to utilize their properties, it is desirable to provide granular superabsorbent polymers in a novel form which offers important improvements and advantages over previous compositions.

It is also desirable to overcome the above described problems and disadvantages of previously known SAP particles and to provide a method of making these SAP particles which is cost effective.

In addition, while numerous attempts to control or modify the particle size have been previously described, there are no direct and convenient methods taught.

Additional features and advantages of the present invention will be set forth in part in the description which follows, and in part will be apparent from the description, or may be learned by practice of the present invention. The objectives and advantages of the invention will be realized and attained by means of the elements, combinations, composition, and process particularly pointed out in the written description and appended claims, as well as the appended drawings and photographs.

To achieve the objects and in accordance with the purpose of the present invention, as embodied and broadly described herein, the present invention relates to an absorbent particle which contains a non-colloidal water resistant solid core which is substantially encapsulated by a hydrogel forming polymer.

The present invention further relates to a process for making these absorbent particles which includes the steps of individually suspending non-colloidal solid particles in a water immiscible solvent in the presence of a surface active agent and then suspending in the water immiscible solvent, an aqueous solution of an ethylenically unsaturated monomer capable of polymerization into a hydrogel forming material, and an initiator. In the next step of the process, the monomer is polymerized such that the non-colloidal solid particles are individually and substantially encapsulated by the hydrogel forming polymer to form absorbent particles. After this polymerization step, the formed absorbent particles are separated from the solvent and dried.

In another aspect of the present invention, there is provided an absorbent composite of hydrophilic fibers and absorbent particles of the present invention.

By providing absorbent particles having a non-colloidal water resistant solid core substantially encapsulated by a hydrogel forming polymer, the physical form and structure of the particles permit the polymer to have a high ratio of surface area to mass, a high rate of fluid absorption, a high level of gel stability, and a high absorbent capacity under load, thereby providing improved absorbent capacity when used in diapers and other absorbent composites and articles.

It is to be understood that both the foregoing general description and the following detailed description are exemplary and explanatory and are intended to provide further explanation of the present invention as claimed.

The accompanying drawings and photographs are included to provide a further understanding of the present invention and are incorporated in and constitute a part of this specification, illustrate various embodiments of the present invention and together with the description serve to explain the principles of the present invention.

DETAILED DESCRIPTION

Reference will now be made in detail to the present invention and various embodiments thereof, examples of which are illustrated in the accompanying drawings.

With respect to the absorbent particle(s) of the present invention, the particle comprises a non-colloidal water resistant solid core substantially encapsulated by a hydrogel forming polymer.

The non-colloidal water resistant solid core serves, in part, as a filler in order to provide a low cost core which is eventually substantially encapsulated by a hydrogel forming polymer. Generally, the size of the solid core, as measured by standard mesh screens, can range from about 10 microns to about 1500 microns, preferably from about 25 microns to about 1000 microns, and more preferably from about 100 microns to about 600 microns. The core can be any shape, e.g., spherical, oval, polyhedral, irregular, and non-spherical.

The weight ratio of filler core to hydrogel forming polymer in the absorbent particle of the present invention is at least about 1:4 and as high as about 9:1, and preferably from about 2:3 to about 2:1.

Typically, each particle of solid core is individually, discretely, and completely contained (i.e., encapsulated) by the hydrogel forming polymer. Occasionally, two or more filler core particles are contained in a single discrete absorbent particle. In some instances, a particle of solid core may not be completely encapsulated, but in most instances, and preferably, the particle of solid core is substantially (e.g., at least about 80% of the surface area of the core is covered with hydrogel forming polymer, preferably at least about 90%, and more preferably at least about 95%), if not completely, encapsulated by the hydrogel forming polymer.

It is to be understood that the term "water resistant" is herein used for purposes of the present invention to mean the non-colloidal solid core is insoluble in water and aqueous solutions and non-swellable (at temperatures below about 90° F.) in water and aqueous solutions yet is wettable with water and aqueous solutions and even preferably wettable with water and aqueous solutions.

Although there is no intention to limit the present invention to any particular non-colloidal, water resistant core filler material, the core filler material can be, for example, one or more materials selected from any of the following groups as long as the core can be encapsulated by the hydrogel forming polymer:

a) water insoluble inorganic minerals including, but not limited to, silicon dioxide, titanium dioxide, magnesium oxide, antimony oxide; clay, talc, wollastonite; synthetic amorphous silica; calcium carbonate; hollow mineral spheres, and the like, including the minerals described in Van Nostrand's Scientific Encyclopedia (1989), Seventh Edition, pages 1864–65 incorporated herein by reference; and b) water insoluble organic materials in particulate or granulated form including but not limited to cereals and cereal components such as hull, bran, flour, germ, and meal; nut shells, wood flour, sawdust, cellulose, microcrystalline cellulose, starch, gelatin, and the like.

Various mixtures and combinations of the foregoing materials can also be used as core filler materials in accordance with the present invention.

With regard to the hydrogel forming polymer, certain preferred water insoluble polymeric compositions useful in the present invention are listed below. Those polymers set forth below and containing acid groups can be, as an option, partially or completely neutralized with alkali metal bases either as the monomer or the polymer or both. While the list below contains many of the preferred polymers which may be used in accordance with the present invention, the present invention is not limited to just these polymers and generally polymers traditionally understood as SAP by those skilled in the art can also be used:

a) polyacrylic acid, polymethacrylic acid, polymaleic acid, copolymers thereof, and alkali metal salts thereof;

b) graft copolymers of starch and acrylic acid, starch and saponified acrylonitrile, starch and saponified ethyl acrylate, and acrylate-vinyl acetate copolymers saponified;

c) polyvinyl alcohol, polyvinylpyrrolidone, polyvinyl aklyether, polyethylene oxide, polyacrylamide, and copolymers thereof;

d) copolymers of maleic anhydride and alkyl vinylethers; and e) saponified starch graft copolymers of acrylonitrile, acrylate esters, vinyl acetate, and starch graft copolymers of acrylic acid, methacrylic acid, and maleic acid.

The above exemplary polymers can be used in their linear state, or optionally, cross-linked either during the polymerization or after the core is encapsulated. This cross-linking can be achieved by methods known to those skilled in the art, including the use of a cross-linking agent. This cross-linking can be initiated in the presence of radiation or a chemical free radial initiator.

Polyfunctional cross-linking agents useful in the present invention include epichlorohydrin and related halo epoxy compounds, diglycidyl ether compounds, diisocyanates, polyaldehydes, and polyfunctional amines and imines.

Polyfunctional ethylenically unsaturated cross-linking agents include N,N',-methylene bisacrylamide, trimethylolpropanetriacrylate, ethylene glycol bismethacrylate, polyethylene glycol bismethacrylate, and divinyl benzene. The use of additional polymer cross-linking agents to modify the properties of gel forming polymers is well known and described in U.S. Pat. No. 4,783,510 as well as by Yin, Y., Polyelectrolyte Gels, Chapter 6, American Chemical Society, 1992, both incorporated herein by reference.

Hydrogel forming polymers and methods of preparation are known in the art and these polymers can be used in the present invention including the polymers set forth in U.S. Pat. Nos. 4,507,438; 5,145,906; 5,196,456; 5,250,642; and 4,295,987 in which divalent cations are used as cross-linking agents, all incorporated herein by reference.

In the present invention, average absorbent particle size and absorbent particle size distribution can be achieved by appropriate selection of the core particle size. Through knowledge of the specific gravity and weight ratio of both the core material and hydrogel forming polymer, the growth in size of the absorbent particle is predictable.

The physical structure of these new particles is new and unique and imparts the desirable properties achieved through this present invention. These include:

1. The absorbent particles are separate and individual and predictable in size by means of the present invention.

2. The great majority of absorbent particles contain one core particle. A minor quantity of absorbent particles contain zero or two core particles.

3. The core particle is centrally located within the absorbent particle.

4. The rigidity and water resistance of the core particle provide an absorbent particle which is high in modulus and gel strength, contributing favorably to the absorbency under load.

5. The particles provide a high ratio of surface area to volume.

For example, an increase of about 50% in the ratio of polymer surface area to polymer volume is realized when comparing a SAP spherical particle of 100% polymer to an example of the current invention in which a spherical particle contains a spherical silica core of 200 µ diameter with a 1:1 weight ratio of SAP to silica.

With regard to methods of making the absorbent particle of the present invention, the following steps can be used:

a) individually suspending non-colloidal water resistant solid particles in a water immiscible solvent in the presence of a surface active agent;

b) suspending in the water immiscible solvent an aqueous solution of an ethylenically unsaturated monomer capable of polymerization into a hydrogel forming material and an initiator;

c) polymerizing the monomer such that the non-colloidal water resistant solid particles are individually and substantially encapsulated by the hydrogel forming polymer to form absorbent particles; and d) separating and drying the absorbent particles.

The hydrogel forming polymer can be cross-linked with polyfunctional cross-linking agents which are included in the aqueous solution in step (b) above. Alternately, polyfunctional cross-linking agents can be added at the end of step (c) and prior to step (d) above. Cross-linking can occur by suspending the absorbent particles in step (d) in a solvent containing a polyfunctional cross-linking agent.

In one preferred aspect of the present invention, the absorbent particle is prepared from partially neutralized sodium acrylate-acrylic acid mixture dissolved in water which is added, along with potassium persulfate (a free radical initiator) to a suspension of silica particles (Ottawa Foundry Sand, Grade F-75, U.S. Silica Company) and surfactant in an organic solvent such as cyclohexane. This particular grade of sand is supplied with a particle size range of from about 50 to about 600 microns with about 85% by weight of the particles in the range of from about 100 to about 200 microns.

Sufficient agitation of the suspension, e.g., with a stirrer, is provided to allow the polymerization mixture to adsorb onto the exterior surface of the core material, e.g., silica particles. The mixture is heated at a temperature of from about 40° C. to about 60° C. for about 2–3 hours to polymerize the sodium acrylate-acrylic acid mixture.

After polymerization is complete, the suspended particles are separated (e.g., by decantation of the liquid components), dried, lightly ground and then classified, e.g., by using a sieve. Prior to separation, azeotropic distillation can be used to remove water from the polymer of the absorbent particles formed.

The average particle size of the resulting absorbent particles of the present invention are preferably in the range of from about 30 microns to about 2000 microns, preferably from about 100 microns to about 600 microns.

Typically from about 90 to about 95% weight yield of absorbent particles are in the size range of from about 100 to about 600 microns. Microscopic examination of the individual particles in the presence of water reveals particles of sand substantially or fully encapsulated by hydrogel forming polymers.

Figure 5:
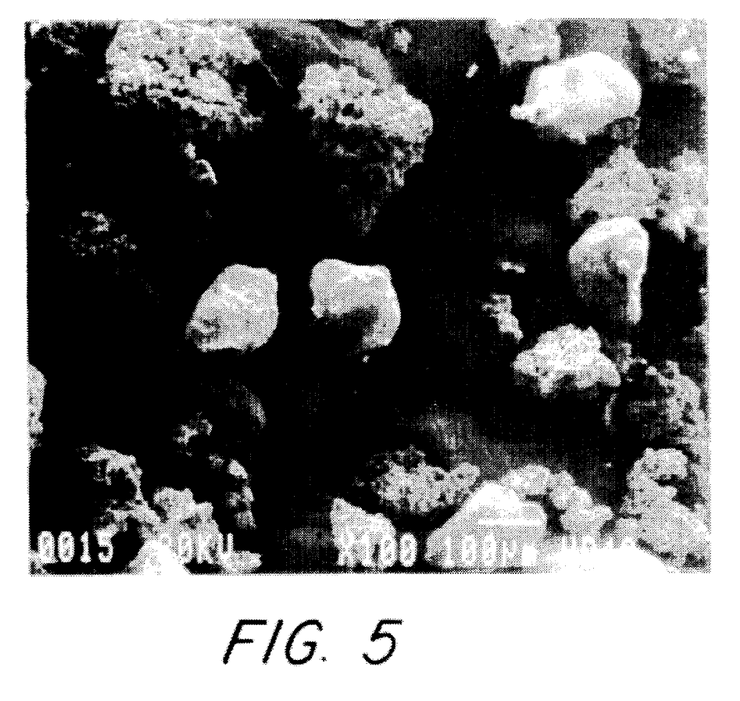
FIGS. 5 and 6 are microphotographs of absorbent particles of the present invention.
Figure 6:
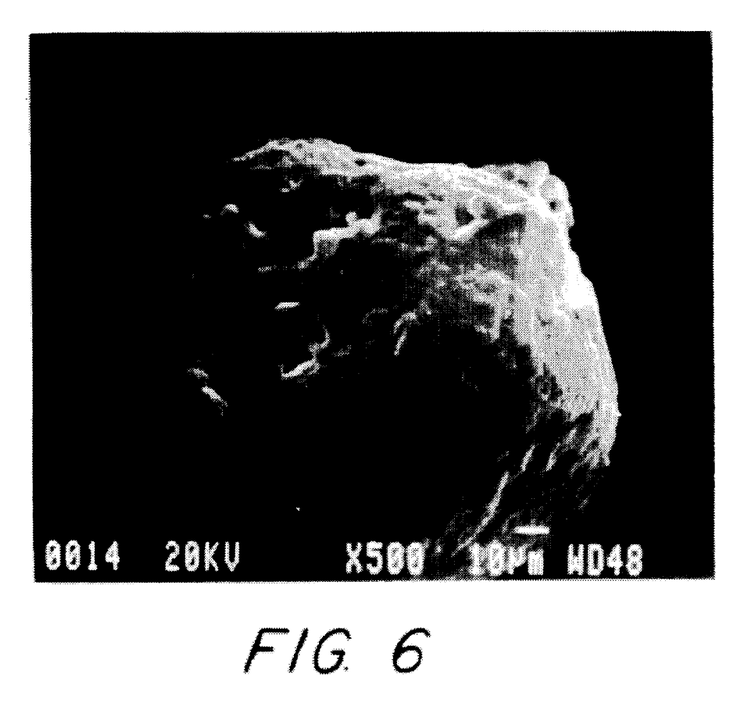

FIG. 5 is a scanning electron micrograph at 100× magnification of an absorbent particle of the present invention in which silica particles (Grade F-75 Ottawa Sand) are coated with a superabsorbent polymer by a method similar to Example 9. FIG. 6 is a 500× magnification of a particle in FIG. 5. The various surface textures from rough to smooth is believed to be due to the degree of particle coalescence as the polymerizing droplets are adsorbed on the inner core.

Depending upon the properties desired in the absorbent particles, the process may be modified by one skilled in the art without undue experimentation with respect to:

a) Particle size distribution of the filler core.
b) Weight ratio of filler core to polymer.
c) Composition of the polymer and cross-link density.
d) Nature and quantity of surfactant.
e) Degree of agitation.
f) Polymerization initiator.

Alternate methods for the preparation of the particles of the present invention are equally useful in that individualization of the non-colloidal solid core particle with subsequent coating by a hydrogel forming polymer is possible. Examples include (1) a fluidized bed of particles in a vapor stream of monomer and initiator under polymerization conditions; and (2) mixing of the non-colloidal particle with monomer and initiator followed by atomization into a chamber which provides the necessary polymerization conditions. It is to be understood that the monomer and initiator are dissolved in a solvent such as water which is subsequently removed upon atomization.

The present invention will be further clarified by the following examples, which are intended to be purely exemplary of the present invention.

EXAMPLES

The absorbent particles of the present invention were compared to a) a superabsorbent particle identified as FAVOR 800 which is commercially available from Stockhausen. FAVOR 800 is believed to be a cross-linked polymer of partially neutralized acrylic acid; and b) a superabsorbent particle identified as ASAP 1000 which is commercially available from Chemdal. ASAP 1000 is also believed to be a cross-linked polymer of partially neutralized acrylic acid.

Example 1

A 1000 ml round bottom flask equipped with nitrogen inlet and outlet tubes, a reflux condenser, a Dean Stark trap, a mechanical stirrer, a thermometer, and an additional funnel were purged with nitrogen. 400 ml of cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the above surfactants were solubilized and the contents of the flask were allowed to cool to room temperature (i.e., approximately 25° C).

Concurrently with the foregoing, 40 ml acrylic acid and 10 ml deionized distilled water were stirred in a 250 ml round bottom flask under a nitrogen atmosphere with cooling provided by an ice bath. While cooling, 16.72 grams of sodium hydroxide dissolved in 50 ml deionized distilled water were added dropwise to the acrylic acid solution. 64 mg of potassium persulfate were then added to the partially neutralized acrylic acid solution. The mixture was stirred for approximately 10 minutes with cooling from the ice bath, then at ambient temperature to complete dissolution of the potassium persulfate and to form a sodium acrylate solution.

40 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 43° C. and held there for 2½ hours. Water was removed as an azeotrope with cyclohexane and the solid dried to give 92.6 grams of off-white granular product.

60 grams of the above product, previously screened through 30 mesh onto 60 mesh, were slurried in 84 ml of methanol. 8.2 ml of 6.8 mg/ml aqueous solution of ethylene glycol diglycidyl ether (56.2 mg) were added. The reaction mixture was heated and stirred at 50°–55° C. for 2 hours. The solvent was removed under reduced pressure and the solid was oven dried at 50° C. to give 62.3 grams of granular product of the present invention containing 44 wt. % silica.

Example 2

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 40 ml of acrylic acid and 10 ml of de-ionized distilled water were stirred in a 250 ml round bottom flask under a nitrogen atmosphere with cooling provided by an ice bath. While cooling, 16.72 grams of sodium hydroxide dissolved in 50 ml de-ionized distilled water were added dropwise to the acrylic acid solution. 64 mg of potassium persulfate were added to the partially neutralized acrylic acid solution. The mixture was stirred for approximately 10 minutes with cooling from the ice bath, then at ambient temperature to complete dissolution of the potassium persulfate and to form a sodium acrylate solution.

62.58 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 43° C. and held there for 2½ hours. Water and cyclohexane azeotrope were distilled off and the solid was dried to give 114.3 grams of off white, granular product.

Example 3

Cross-Linked 36.5 grams, previously screened through 30 mesh onto 60 mesh, of the granular product of Example 2 was slurried in 35 ml of methanol. 4.0 ml of 6.8 mg/ml aqueous solution of ethylene glycol diglycidyl ether (27.44 mg) were added. The reaction mixture was heated and stirred at 50–55° C. for 2 hours. The solvent was removed under reduced pressure and the solid was oven dried at 50° C. to give 37.3 grams of granular product with 55 wt. % of silica.

Example 4

Example 4 was prepared in a manner similar to the procedure of Example 1. The core material was Hubercarb grade Q20–60 (J-W Huber Corporation, St. Louis, Mo.) comprised typically of 96.5% calcium carbonate (2% by weight of the size of calcium carbonate was 1170 microns–1560 microns), 2.0% magnesium carbonate, and 1.2% silica. The particle size distribution was characterized as 90% (by weight) greater than 200 microns and 10% (by weight) greater than 900 microns with a median particle size of about 450 microns. The weight ratio was 45 parts filler to 55 parts polymer. Example 4 was prepared without cross-linking agents.

Example 5

Example 5 was a repeat of Example 1 except that after removal of 44 gm of water as an azeotrope, 15.4 mg of ethylene glycol diglycidyl ether in 5 ml of methanol were added and the reaction mixture held for 3 hours at 50° C. At the end of this time, the remainder of the water was removed by azeotropic distillation (10 ml). The granular product was recovered and dried in an oven at 65° C. for 4 hours.

Example 6

The objective of Example 6 was to increase the ratio of core filler to 72% by weight. Accordingly, a 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 548 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 20 ml acrylic acid and 10 ml deionized distilled water were stirred in a 250 ml round bottom flask under nitrogen atmosphere with cooling provided by an ice bath. While cooling, 8.36 grams of sodium hydroxide dissolved in 50 ml deionized distilled water were added dropwise to the acrylic acid solution. 33 mg potassium persulfate were added to the partially neutralized acrylic acid solution. The mixture was then stirred for approximately 10 minutes with cooling from the ice bath, then at ambient temperature to complete dissolution of the potassium persulfate and to form a sodium acrylate solution.

40 grams of Ottawa fine foundry sand (Grade F-75) with an AFS grain size of 75 were added to the cyclohexane/surfactant solution. The sodium acrylate solution was added with vigorous stirring. The temperature of the reaction mixture was brought to 55° C. and held there for 2½ hours. 41 ml of water was removed as an azeotrope with cyclohexane. At that point, 15.4 mg of ethylene glycol diglycidyl ether in 4.8 ml of methanol was added and the reaction mixture held for 3 hours at 50° C. The reaction mixture was cooled to room temperature overnight.

The reaction was heated and an additional 12 ml water removed by azeotropic distillation. The reaction mixture contains some granular solid and some solid adhering to the wall of the flask. The granular product was recovered and dried in an oven at 50° C. overnight. Deionized distilled water was added to the flask to swell off the solid adhering to the wall of the flask. The material was collected in a glass dish and allowed to dry. The solid exists as a mixture of small granules and larger ½-inch agglomerates.

Example 7

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 549 mg of polyoxyethylene 5 sorbitan monooleate (available as TWEEN 81® from ICI Americas, Inc., Wilmington, Del.), and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

Meanwhile, 40 ml acrylic acid and 10 ml deionized distilled water were stirred in a 250 ml round bottom flask under nitrogen atmosphere with cooling provided by an ice bath. While cooling, 16.72 grams of sodium hydroxide dissolved in 50 ml deionized distilled water were added dropwise to the acrylic acid solution. 64 mg potassium persulfate were then added to the partially neutralized acrylic acid solution. The mixture was stirred for approximately 10 minutes with cooling from the ice bath, then at ambient temperature to complete dissolution of the potassium persulfate and to form a sodium acrylate solution.

27.5 gm of corn bran (Illinois Cereal Mills lot 99C-30) were added to the cyclohexane/surfactant solution. The sodium acrylate solution was then added with vigorous stirring. The temperature of the reaction mixture was brought to 55° C. and held there for 2½ hours. 43 gms of water were removed as an azeotrope with cyclohexane. A particulate phase and a fused phase were both present at the end of this time. The solid phase was removed (approximately 35 gm of material). At that point, 4.3 ml of solution containing 8.5 mg ethylene glycol diglycidyl ether were added to the reaction mixture and the reaction mixture held for 3 hours at 50° C. At the end of this time, the remainder of the water was removed by azeotropic distillation (10 ml). The granular product was recovered and dried in an oven at 65° C. for 4 hours.

Example 8

In Example 8, 4.0 gm of material prepared in the same manner as Example 6 were placed in a 50 ml flask along with 5.0 ml methanol plus 0.55 ml of a solution of ethylene glycol diglycidyl ether in methanol (10 mg/ml). The mixture was stirred at 55° C. for 2 hours and then separated and dried.

Example 9

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 550 mg of polyoxyethylene 5 sorbitan monooleate (available as TWEEN 81® from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

At the same time, 40 ml acrylic acid and 10 ml deionized distilled water were stirred in a 250 ml round bottom flask under nitrogen atmosphere with cooling provided by an ice bath. While cooling, 16.72 grams of sodium hydroxide dissolved in 50 ml deionized distilled water were added dropwise to the acrylic acid solution. 64 mg potassium persulfate were added to the partial neutralized acrylic acid solution. The mixture was stirred for approximately 10 minutes with cooling from the ice bath, then at ambient temperature to complete dissolution of the potassium persulfate to form a sodium acrylate solution.

51.2 grams of Ottawa fine foundry sand (Grade F-75) with an AFS grain size of 75 were added to the cyclohexane/surfactant solution. The sodium acrylate solution was then added with vigorous stirring. The temperature of the reaction mixture was brought to 54° C. and held there for 2½ hours. Water was removed as an azeotrope with cyclohexane. 21 gms of water was removed as an azeotrope with cyclohexane. A particulate phase had formed at this point. At that point 3.4 ml of a methanol solution containing 10.2 mg ethylene glycol diglycidyl ether were added and the reaction mixture held for 2 hours at 50° C. Next, 23 ml of water was removed by azeotropic distillation. At that point another 3.4 ml of a methanol solution containing 10.2 mg ethylene glycol diglycidyl ether were added and the reaction mixture held for 2 more hours at 50° C. At the end of this time, the remainder of the water was removed by azeotropic distillation (14 ml). The granular product was recovered and dried in an oven at 65° C. for 4 hours. The total yield was 103.2 gm.

Example 10

A 1000 ml round bottom flask equipped with nitrogen inlet and outlet tubes, a reflux condenser, a Dean Stark trap, a mechanical stirrer, a thermometer, and an addition funnel were purged with nitrogen. 400 ml of cyclohexane, 550 mg of polyoxyethylene 5 sorbitan monooleate (available as TWEEN 81™ from ICI Americas, Inc., Wilmington, Del.) and 540 mg of sorbitan monostearate (available as SPAN 60® from ICI Americas, Inc., Wilmington, Del.) were added to the flask and the internal temperature brought to 42° C. with stirring to disperse the sorbitan monostearate. After approximately 10 minutes, the contents of the flask were allowed to cool to room temperature.

At the same time, 40 ml acrylic acid and 10 ml deionized distilled water were stirred in a 250 ml round bottom flask under nitrogen atmosphere and with cooling provided by an ice bath. While cooling, 16.72 grams of sodium hydroxide dissolved in 50 ml deionized distilled water were added dropwise to the acrylic acid solution. 64 mg potassium persulfate were added to the partially neutralized acrylic acid solution. The mixture was stirred for approximately 10 minutes with cooling from the ice bath, then stirred at ambient temperature to complete dissolution of the potassium persulfate and form a sodium acrylate solution.

30 gms of corn starch (Argo brand) were added to the cyclohexane/surfactant solution. The sodium acrylate solution was added with vigorous stirring. The temperature of the reaction mixture was brought to 55° C. and held there for 2½ hours. 42 gms of water were removed as an azeotrope with cyclohexane. A particulate phase has formed at this point. At that point 5.2 ml of a methanol solution containing 15.4 mg ethylene glycol diglycidyl ether were added and the reaction mixture held for 3 hours at 50° C. At the end of this time, the remainder of the water was removed by azeotropic distillation (16 ml). The granular product was recovered and dried in an oven at 65° C. for 4 hours. The total yield was 82.9 gm.

Example 11

In Example 11, 4.0 gm of material prepared in the same manner as Example 1 were placed in a 50 ml flask along with 5.0 ml methanol plus 0.55 ml of a solution of ethylene glycol diglycidyl ether in methanol (10 mg/ml). The mixture was stirred at 55° C. for 2 hours and then separated and dried.

Test Procedures

1. Swell Time to Gel
A sample is passed through U.S. 30 Screen and collected on U.S. 60 mesh. A test specimen, 0.25gm, is placed in a 7.0 ml vial. Add 2.5 gm of 1.0% sodium chloride. Observe and record time for meniscus to disappear as sample gels.
2. Capacity Place 0.3 gm on aluminum pan and weigh. Add 10 ml of 1% saline solution; cover with film and let stand for 1½ hours. Discard excess solution and weigh. Calculate:

$$\frac{\text{(wt. of absorbent particle + saline)} - \text{wt. of absorbent particle}}{\text{wt. of absorbent particle}}$$

Absorbency Under an External Load

Purpose

Determine the amount of fluid absorbed by absorbent materials while placed under an external load as a function of time.

Conditions

A 0.016 gram sample of absorbent material is placed on a 20.28 cm$^2$ area, and a pressure of 21,000 dynes/cm$^2$ (approximately 0.3 lb/in$^2$) is applied.

Equipment

Electronic Balance (range: minimum of 200 g; accuracy: at least 0.001 g) 2.54 cm (1 inch) inner diameter (I.D.) cylinder (material: Plexiglass®) with a stainless steel screen (mesh: 100) fused to the cylinder bottom. 2.5273 cm (0.995 inch) piston (material: Plexiglass®) weighing 4.4 g. 100 g weight (balance calibration weight).

Timer Controlled Atmosphere: Temperature 23° C. (73.4° F.) Relative Humidity 50%

Procedure

1. Prepare 1 kg of 0.9% (w/w) NaCl solution or synthetic urine.

2. Screen absorbent material to a 30/60 cut and place the 30/60 cut of material in sealed storage containers to maintain constant product conditions.

3. Place 0.160 g of absorbent material onto pre-tared weighing paper. Record the actual absorbent material weight, $W_f$, on a record sheet.

4. Slowly add the absorbent material into the cylinder with the screened bottom.

5. Gently tap the cylinder until the material is evenly distributed on the mesh. If absorbent material is on cylinder wall, the test is re-run.

6. Place piston into cylinder.

7. Place 100 g weight on piston.

8. Weigh the combined cylinder, piston and test material. Record this weight, $W_c$, on the record sheet.

9. Pour thin layer of solution into pan.

10. Place filter paper into pan and allow the solution to saturate the filter paper.

11. Set timer for predetermined time interval (1 or 5 minutes) or a maximum time (i.e. 60 minutes). (Measurements conducted at various time intervals are used to calculate and develop an absorption curve for the absorbent material.)

12. Place the combined cylinder on the saturated filter paper and simultaneously start the timer.

13. Upon expiration of time, remove the combined cylinder and blot on paper toweling.

14. Weigh the combined cylinder. Record this weight $W_s t$, on the record sheet.

15. Repeat steps 11 through 14 until equilibrium is reached or a maximum test time is obtained. Expand the time interval as maximum absorbency is approached. A suggested interval sequence is 0, 1, 2, 5, 10, 30, 60, and 90 minutes.

16. Measure the displaced piston height from the bottom of the cylinder. Record this height H on the record sheet.

17. Upon completion of the absorbency test, remove the piston and observe the condition of the material. Record the observation on the record sheet.

Calculations $W_f$ Weight of the absorbent material $W_c$ Dry weight of the combined cylinder $W_s t$ Wet weight of the combined cylinder at time, t $A_t$ Material absorbency under an external load at time, t A Maximum material absorbency under load.

Absorbency under an external load $$At = \frac{W_s t - W_c}{W_f}$$

$$A = (\max A^t)$$

The absorbency properties of representative examples of the present invention are shown below in Tables I and II.

Properties

In Example 1, F-75, a fine foundry sand, was covered with a preferred hydrogel forming polymer prepared from an aqueous solution of partially neutralized acrylic acid at a weight ratio of 45 parts filler core to 55 parts polymer.

Example 3 differed from Example 1 in weight ratio by using 55 parts filler core to 45 parts polymer. In Example 2, the polymer was not cross-linked and differed from Example 3 which was cross-linked.

TABLE I

| Absorbent Particle | Maximum Swell Capacity g saline/g | Swell Time to Gel seconds 10:1 |
| --- | --- | --- |
| Favor 800 (Stockhausen) | 47 | 25 |
| ASAP 1000 (Chemdal) | 40 | 29 |
| Example Number | | |
| 1. | 27 | 14 |
| 2. | 50+ | 32 |
| 3. | 23 | 24 |
| 4. | 40+ | 120 |
| 5. | 70+ | 9 |
| 6. | 70+ | 44 |
| 7. | 70+ | 85 |
| 8. | 25 | 27 |
| 9. | 41 | 4 |
| 10. | 70+ | 28 |

TABLE II

| | Absorbency Under Load gm saline (1.0%) per gm | | | | |
| --- | --- | --- | --- | --- | --- |
| | 1 minute | 5 minutes | 10 minutes | 20 minutes | 30 minutes |
| Example 1 | 11 | 13 | 14 | 15 | — |
| Example 3 | 10 | 14 | 16 | 16 | 16 |
| Favor 800 | 7 | 11 | 15 | 20 | 23 |
| ASAP 1000 | 8 | 16 | 20 | 22 | — |
| Example 8 | 6 | 11 | 11 | 12 | 12 |
| Example 9 | 5 | 5 | 6 | 6 | 7 |
| Example 10 | 5 | 6 | 6 | 7 | |
| Example 11 | 10 | 18 | 20 | 21 | 22 |

The highly competitive performance in rate and absorbency under a load of the product of the present invention as seen from the data in Table II are unexpected and represent an important advance in the art.

The complete adsorption of the polymerizing droplets onto the surface of the filler core was surprising and unexpected. During the course of the preparation it appeared that the filler particles became encapsulated during the early stages of the polymerization. This suggests certain theoretical explanations for the complete adsorption mentioned above. For example, early in the initiation of the polymerization, the soft and perhaps "sticky" droplets are attached to the filler core surface by secondary chemical forces or bonding provided at least in part by the chemical nature of the filler core particle surface. Additionally, the core particle surface may provide a sufficiently high surface energy to be readily wetted by the polymerizing droplets. In general, those physical-chemical phenomenon that tend to effect or control the adsorption and heterogenous reactions of liquids on solid surfaces influence the desired formation of the encapsulated core particles.

Absorbent Cores of Fiber and Superabsorbent Particles

Examples 12–16

Cellulose pulp fibers were mixed with superabsorbent particles in a laboratory machine capable of providing a suitable air stream and collection screen to collect the mixture in the form of a soft, fluffy web.

Figure 1:
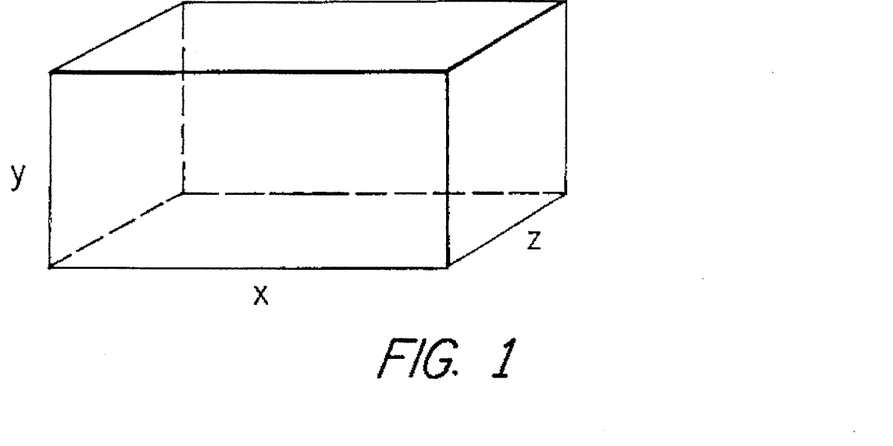
FIG. 1 is a diagrammatic representation of an absorbent core in accordance with the present invention.

FIG. 1 illustrates an absorbent core with a volume defined by the x, y, and z axis.

Figure 2:
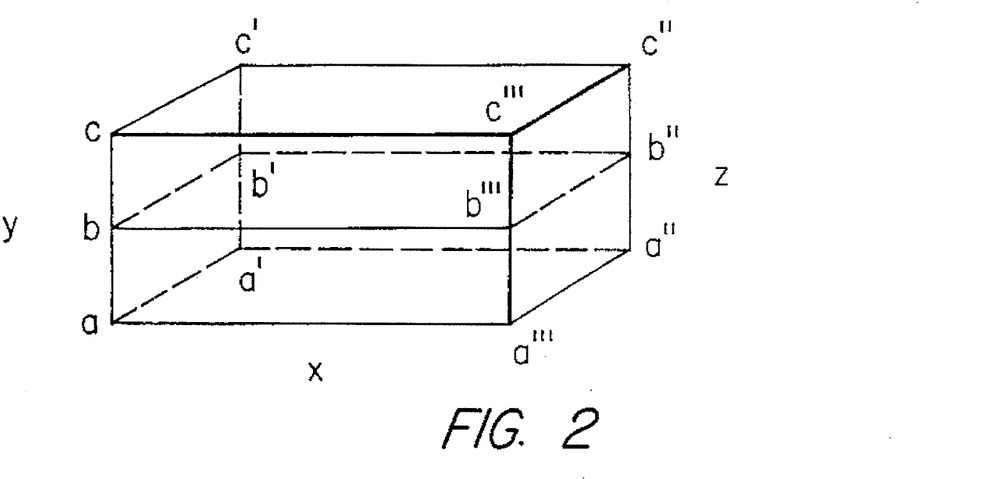
FIGS. 2–4 are diagrammatic representations of absorbent cores in accordance with the present invention showing various volumetric zones.

In FIG. 2, two volumetric zones are defined, one by the boundaries ab, a'b', a"b", and a''', b''' and a second by bc, b'c', b"c", and b'''c'''.

Figure 3:
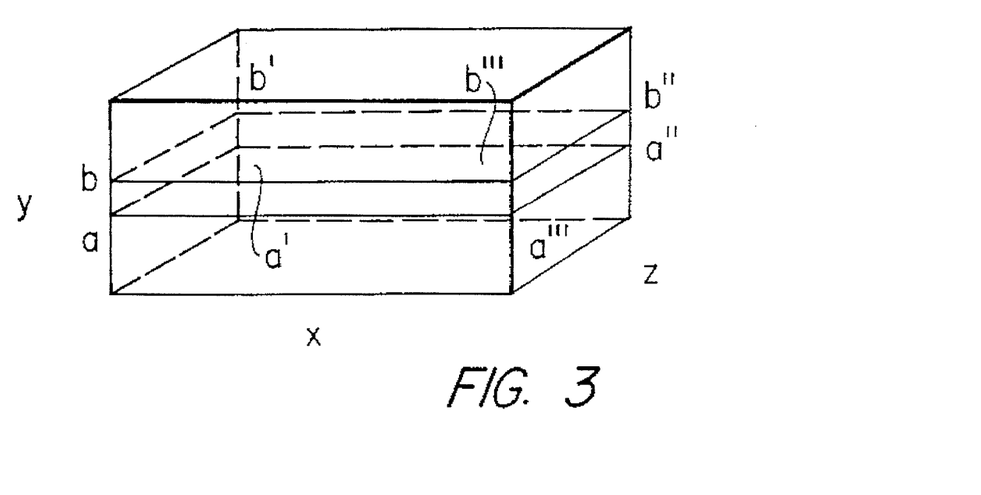
Figure 4:
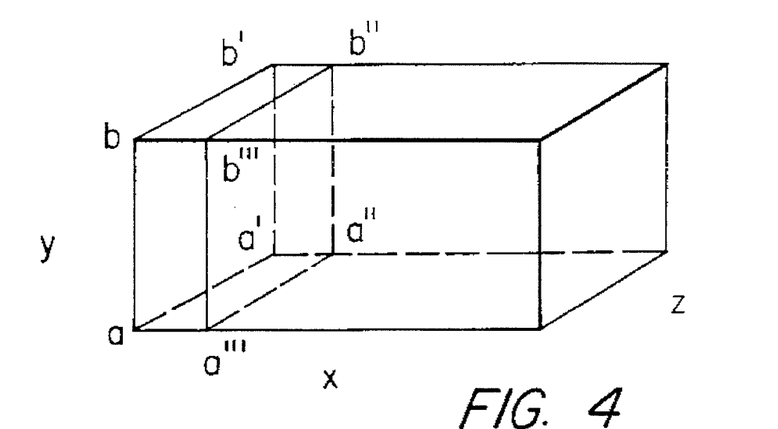

In FIGS. 3 and 4, the volumetric zone ab, a'b', a"b", and a'''b''' is defined.

The web of fiber and particles referred to herein as absorbent cores were approximately 9 inches in length, 4 inches in width, and after compression in a hydraulic press, 0.25 inch thickness. Referring to FIGS. 1 and 2, these dimensions are represented in an absorbent core by length "x," width "y," and thickness "z," respectively.

The absorbent cores of the present invention are defined by a series of planes, each of which is formed by the intersection of lines x and y moving in the z direction. These planes or any combination of multiples of planes provide volumetric zones (e.g., referring to FIG. 3, showing a volumetric zone ab, a'b', a"b", a'''b''' and FIG. 4 showing a zone ab, a'b', a"b", a'''b''') which are comprised of fiber, particles of the present invention, and air. These zones can occupy at least about 2% of the volume of an absorbent device in the dry state. Since the absorbent particles of the present invention are each individually comprised of a filler core and a superabsorbent polymer in the weight range of preferably about 30 to 70 to 70 to 30, it follows that the aforementioned volumetric zones are comprised of four components; namely, fiber, air, superabsorbent polymer, and filler. Furthermore, these components may be varied in both ratio and location in the core, thus providing a new degree of freedom in design of absorbent cores which may be optimized for both functionality and cost. The foregoing discussion on the particle composition and other variables associated with the particles of the present invention clearly shows the enormous magnitude of design options available with this new particle in combination with fiber and void space in the absorbent core.

Table III lists the composition and properties of several examples of absorbent cores containing a) pulp fibers; and b) SAP and/or absorbent particles of the present invention.

From the data in Table III, it is shown that with the absorbent particles of the present invention, it is now possible to more closely optimize cost and performance in an absorbent device particularly with respect to performance attributes of capacity and rate.

More specifically, the data in Table III provides the basis for the design of absorbent devices with unique and heretofore unachievable properties without significant cost increases.

Figure 7:
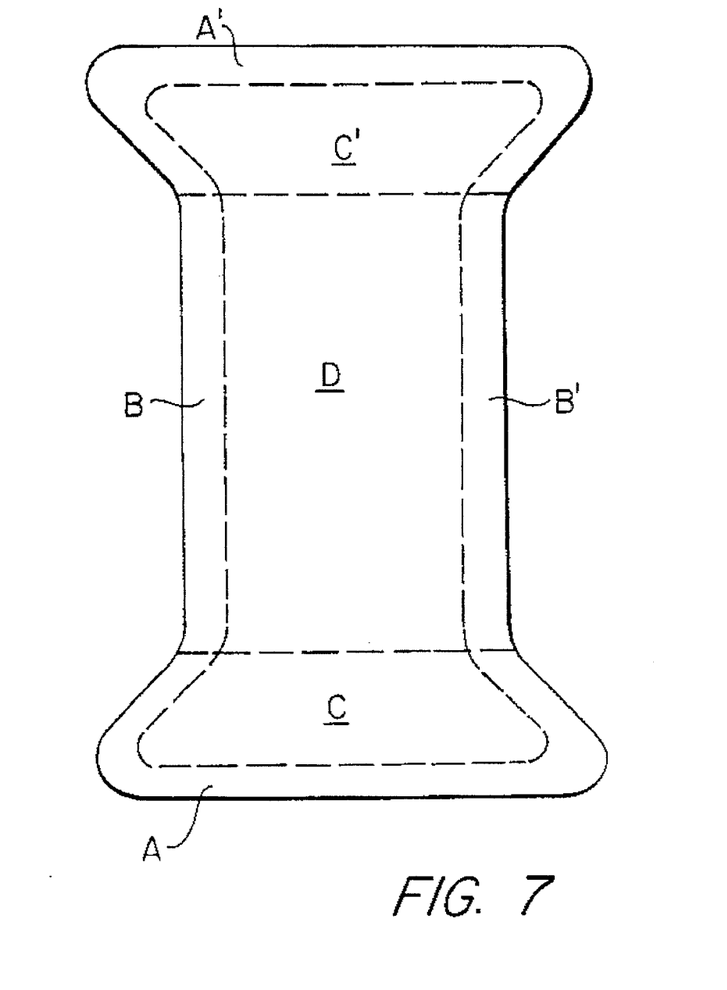
FIG. 7 is a diagrammatic representation of an absorbent device showing various zones.

For example, in the device shown in FIG. 7, a number of zones are indicated, each of which may have special importance due to location, in providing the desired functions of leakage prevention, providing a dry surface to the wearer, and reduction in bulk through replacement of pulp with SAP particles; and, importantly to achieve these at low cost.

The absorbent core of Example 14 contains 8.1 gm of SAP particles of which 1.6 gm are 100% superabsorbent polymer ASAP 1000. The remaining 6.5 gm of particles (Example 1) contain 56% SAP by weight or 3.6 gm SAP giving a total amount of SAP of 5.2 gm. In comparison with Example 12 which contains 9.0 gms of superabsorbent, the rate of absorption and surface dryness are significantly improved for the rate of absorption and roughly equivalent for surface dryness. These improvements are achieved at a significant reduction in raw material cost.

Absorbent devices such as that shown in FIG. 7 may thus be optimized by the presently disclosed particles by employing, e.g., 75–100% more absorbent particles in, for example, zones A,A', B,B', and optionally C,C' thus achieving major improvements in leakage prevention through the presence of more available SAP surface area (i.e., a greater number of absorbent particles of the present invention can be made with the same amount of SAP used in present commercial absorbent devices).

Alternatively, an absorbent device of FIG. 7 may be designed with high capacity particles as in Example 5 and located in the more inward zone D where control of large amounts of localized fluid is needed. As in the discussion above, such an improvement can be achieved without additional cost by using increased amounts of the lower cost particles of the present invention.

The absorbent particles of the present invention can be used in all types of absorbent devices where commercially available SAP particles are used. The absorbent particles of the present invention can fully or partially replace the

TABLE III

| | | | Absorbent Core Properties | | | | | | |
|---|---|---|---|---|---|---|---|---|---|
| | Absorbent Core Wt | Wt % SAP and/or Absorbent | SAP and/or Particle | Time to Absorb 40 ml Saline, Successive Insults Seconds | | | | Rewet | Capacity |
| Ex. | (gms) | Particle | Composition | 1 | 2 | 3 | 4 | (gm) | (gm) |
| 12 | 18.0 | 50 | ASAP-1000 | 8 | 21 | 55 | 90 | 7.6 | — |
| 13 | 19.5 | 30 | ASAP-1000 | 6 | 11 | 27 | 40 | 8.5 | — |
| 14 | 20.3 | 40 | Example 1 (4 pbw) ASAP-1000 (1 pbw) | 7 | 21 | 31 | 53 | 7.7 | |
| 15 | 18.8 | 40 | ASAP-1000 | — | — | — | — | — | 363 |
| 16 | 19.1 | 40 | Example 1 (4 pbw) ASAP-1000 (1 pbw) | — | — | — | — | — | 337 | commercially available SAP particles in absorbent devices such as those described in U.S. Pat. Nos. 5,019,063; 5,300,358; 4,324,247; 4,342,314; 4,634,440; 5,074,856; and 4,944,735, all incorporated herein by reference in their entireties.

As shown in Table III, for example, particles of the present invention can be blended with commercially available superabsorbent polymers to achieve a wide range of cost and performance. For instance, commercially available SAP particles can be combined with absorbent particles of the present invention in weight ratios of from about 1:9 to about 9:1. In addition, when the absorbent particles are used in an absorbent device such as a diaper or sanitary napkin, the hydrophilic fibers and absorbent particles are present in a weight ratio of from about 95:5 to about 2:3.

Techniques to increase the ratio of surface area to mass by forming aggregates of small SAP particles as taught, for example, in U.S. Pat. No. 5,180,622 (Berg), or by incorporating blowing agents as for example in U.S. Pat. No. 5,118,719 (both incorporated herein by reference) are applicable to the present invention as well with the added advantage of significantly reduced cost due to the filler core.

Example 17

A portion of the product from Example 5 remaining on a #30 mesh screen was ground lightly with a mortar and pestle and then combined with the portion that had passed through the screen. Using Nos. 30, 60, and 140 mesh screens, the particle size distribution of the combined material was determined and compared to the F-75 silica core material. This comparison shown in Table IV clearly illustrates the high degree of predictability of particle size offered by the present invention.

TABLE IV

|  | Silica F-75, Wt. % | Example 5, Wt. % |
| --- | --- | --- |
| Less than 100 microns | 7 | 10 |
| Less than 150, greater than 100 microns | 22 | — |
| Greater than 150, less than 300 microns | 65 | — |
| Greater than 300 microns | 6 | — |
| Greater than 100, less than 260 microns | — | 26 |
| Greater than 260, less than 700 microns | — | 64 |

Of course, various stabilizers, dispersants, dyes, pigments, diluents and the like, as well as anti-microbial agents, odor absorbing compounds, and perfumes can be part of the absorbent particle of the present invention.

Other embodiments of the present invention will be apparent to those skilled in the art from consideration of the specification and practice of the present invention disclosed herein. It is intended that the specification and examples be considered as exemplary only, with a true scope and spirit of the present invention being indicated by the following claims.

What is claimed is:

1. A method for preparing absorbent particles, comprising the steps of:
    a) suspending water resistant solid particles in a water immiscible solvent in the presence of a surface active agent;
    b) suspending in said water immiscible solvent an aqueous solution of an ethylenically unsaturated monomer capable of polymerization into a hydrogel forming polymer and an initiator;
    c) polymerizing said monomer such that said water resistant solid particles are individually and substantially encapsulated by said hydrogel forming polymer to form absorbent particles; and
    d) separating and drying said absorbent particles.

2. The method of claim 1, wherein said hydrogel forming polymer is cross-linked with a polyfunctional cross-linking agent which is included in the aqueous solution in step (b).

3. The method of claim 1, wherein the aqueous solution further comprises a polyfunctional cross-linking agent.

4. The method of claim 11, wherein said hydrogel forming polymer is cross-linked with a polyfunctional cross-linking agent which is added at the end of step (c) and prior to step (d).

5. The method of claim 1, wherein said absorbent particles in step (d) are cross-linked by suspending said absorbent particles in a solvent containing a polyfunctional cross-linking agent.

6. The method of claim 1, wherein the water resistant solid particles have a size of from about 10 microns to about 1500 microns.

7. The method of claim 1, wherein the weight ratio of the water resistant solid particles to hydrogel forming polymer is from about 1:4 to about 9:1.

8. The method of claim 1, wherein the average particle size of the absorbent particles is in the range of from about microns to about 2000 microns.

9. The method of claim 1, wherein the water resistant solid particles are cereal, starch, cellulose, or gelatin in particulate form.

10. The method of claim 1, wherein at least two absorbent particles are attached through interparticle surface bonding with an average particle size of from about 30 to about 1500 microns.

11. The method of claim 1, wherein said water immiscible solvent is an organic solvent.

12. The method of claim 1, wherein said water immiscible solvent is cyclohexane.

13. The method of claim 1, wherein said initiator is potassium persulfate.

14. The method of claim 1, wherein said surface active agent is polyoxyethylene 5 sorbitan monooleate, sorbitan monostearate, or a mixture thereof.

15. The method of claim 1, wherein said monomer is acrylic acid.

16. The method of claim 1, wherein said water resistant solid particles are sand.

17. The method of claim 1, wherein said monomer is acrylic acid, said water resistant solid particles are silica, and said solvent is cyclohexane.

18. The method of claim 1, wherein the water resistant solid particles are inorganic minerals.

19. The method of claim 18, wherein the inorganic minerals are silicon dioxide, titanium dioxide, magnesium oxide, antimony oxide, clay, talc, wollastonite, synthetic amorphous silica, or calcium carbonate.

20. The method of claim 1, wherein said hydrogel forming polymer is selected from the group consisting of polyacrylic acid, polymethacrylic acid, polymaleic acid and copolymers thereof, and their alkali metal salts; polyvinyl alcohol, polyvinyl pyrrolidone; polyvinyl alkylether, polyethylene oxide polyacrylamide and copolymers thereof; saponified starch graft copolymers of acrylonitrile, acrylate esters, vinyl acetate; starch graft copolymers of acrylic acid, methacrylic acid, and maleic acid; and copolymers of maleic anhydride and alkyl vinyl ethers.

21. The method of claim 10, wherein the hydrogel forming polymer is cross-linked with a polyfunctional epoxy, haloepoxy, aldehyde, amine, imine, or isocyanate compound or by a polyfunctional ethylenically unsaturated compound.

* * * * *

UNITED STATES PATENT AND TRADEMARK OFFICE
CERTIFICATE OF CORRECTION

PATENT NO. : 5,539,019
DATED : July 23, 1996
INVENTOR(S) : Stuart Suskind et al.

It is certified that error appears in the above-identified patent and that said Letters Patent is hereby corrected as shown below:

Title Page

Item [75], inventors information; line 2, delete "1441 Waverly Ave." and line 3, delete "19035".

Claim 4, column 18, line 9, delete "11" and insert --1--.

Claim 8, column 18, line 24, before "microns" (first occurrence), insert --30--.

Claim 20, column 18, line 57, after "oxide", insert --,--.

Signed and Sealed this

Twenty-ninth Day of October 1996

Attest:

BRUCE LEHMAN

*Attesting Officer*  *Commissioner of Patents and Trademarks*